United States Patent [19]
Himmel et al.

[11] Patent Number: 6,013,860
[45] Date of Patent: Jan. 11, 2000

[54] EXPRESSION OF ENZYMES INVOLVED IN CELLULOSE MODIFICATION

[75] Inventors: Michael E. Himmel, Littleton, Colo.; David J. Schaaf, Davis; David M. Stalker, Woodland, both of Calif.; Steven R. Thomas, Denver, Colo.

[73] Assignee: Calgene LLC, Davis, Calif.

[21] Appl. No.: 09/122,533

[22] Filed: Jul. 24, 1998

[51] Int. Cl.[7] .............................. C12N 15/82; C12N 5/04; C07H 21/04; C07H 21/02

[52] U.S. Cl. .......................... 800/278; 435/69.1; 435/468; 435/410; 435/419; 435/320.1; 435/209; 536/23.1; 536/23.7; 800/284; 800/288; 800/290; 800/295

[58] Field of Search ................................... 435/69.1, 468, 435/410, 419, 320.1, 209; 536/23.1, 23.7; 800/278, 284, 288, 290, 295

[56] References Cited

U.S. PATENT DOCUMENTS

| | | |
|---|---|---|
| 5,015,580 | 5/1991 | Christou et al. . |
| 5,275,944 | 1/1994 | Himmel et al. . |
| 5,416,011 | 5/1995 | Hinchee et al. . |
| 5,536,655 | 7/1996 | Thomas et al. . |
| 5,576,198 | 11/1996 | McBride et al. . |

FOREIGN PATENT DOCUMENTS

| | | |
|---|---|---|
| WO 92/15675 | 9/1992 | WIPO . |
| WO 98/11235 | 3/1998 | WIPO . |

OTHER PUBLICATIONS

Kawazu, et al., "Expression of the Rumen Cellulase Gene in Tobacco Enhances Plant Cell Wall Digestion" Abstracts of Papers: 213th ACS National Meeting, Cell 101, (1997).

Svab, et al., "High–frequency Plastid Transformation in Tobacco by Selection for a Chimeric aadA Gene" *Proceedings of the National Academy of Sciences of the USA* 90, pp. 913–917 (1993).

Zoubenko, et al., "Efficient Targeting of Foreign Genes into the Tobacco Plastid Genome" *Nucleic Acids Research* 22(19), pp. 3819–3824, (1994).

Shinozaki, et al., "The Complete Nucleotide Sequence of the Tobacco Chloroplast Genome: its Gene Organization and Expression" *EMBO Journal* 5(9), pp. 2043–2049 (1986).

Chrispeels, et al., "Short Peptide Domains Target Proteins to Plant Vacuoles" *Cell* 68, pp. 613–616 (1992).

Staub, et al., "Accumulation of D1 Polypeptide in Tobacco Plastids is Regulated via the Untranslated Region of the psbA mRNA" *The EMBO Journal* 12(2), pp. 601–606 (1993).

Klein, et al., "Transformation of Microbes, Plants and Animals by Particle Bombardment" *Bio/Technology* 10, pp. 286–291(1992).

McBride, et al., "Controlled Expression of Plastid Transgenes in Plants Based on a Nuclear DNA–encoded and Plastid–targeted T7 RNA Polymerase" *Proceedings of the National Academy of Sciences of the USA* 91, pp. 7301–7305 (1994).

Svab, et al., "Stable Transformation of Plastids in Higher Plants" *Proceedings of the National Academy of Sciences of the USA* 87, pp. 8526–8530 (1990).

Mohagheahi, et al., "Isolation and characterization of *Acidothermus cellulolyticus* gen. Nov., sp. Nov., a New Genus of Thermophilic, Acidophilic, Cellulolytic Bacteria" *International Journal of Systemic Bacteriology* 36(3), pp. 435–443 (1986).

Sakon, et al., "Crystal Structure of Thermostable Family 5 Endocellulase E1 from *Acidothermus celluloyticus* in Complex with Cellotetraose" *Biochemistry* 35, pp. 10648–10660 (1996).

Wilson, et al. "Biochemistry and Genetics of Actinomycete Cellulases" *Critical Reviews in Biotechnology* 12(1/2), pp. 45–63 (1992).

Henrissat, et al., "Updating the Sequence–based Classification of Glycosyl Hydrolases" *Biochemical Journal* 316, pp. 695–696 (1996).

*Primary Examiner*—Elizabeth F. McElwain
*Assistant Examiner*—Ousama M-Faiz Zaghmout

[57] ABSTRACT

Novel compositions and methods useful for genetic engineering of plant cells to provide expression in the plastids of a plant or plant cell of cellulose degrading enzymes.

26 Claims, 3 Drawing Sheets

EXPRESSION OF ENZYMES INVOLVED IN CELLULOSE MODIFICATION

TECHNICAL FIELD

This invention relates to the application of genetic engineering techniques to plants. More specifically, the invention relates to compositions and methods for expressing polysaccharide hydrolyzing enzymes (cellulases, cellobiohydrohrolases, xylanases, hemicellulases) in plant plastids.

BACKGROUND

Cellulases (β-1,4-endoglucanase) are a family of enzymes that work together to break down cellulose to its simple sugar components. Cellulose may also be degraded via acid hydrolysis using much harsher conditions than required by cellulase enzymes. Furthermore, cellulases catalyze highly specific reactions, yeilding specific products, and are required in much smaller quantities compared to acid hydrolysis reactions.

Cellulose degrading enzymes are used for a wide variety of industrial applications. One of the major potential uses of cellulase is in the conversion of cellulosic biomass to industrially important end products (ie; sugars, which can be fermented to produce a variety of products). For example, production of fuel ethanol is typically produced from grains such as corn. A similar process utilizing high cellulosic rice straws is currently under development. Unfortunately, ethanol produced by such methods is still too expensive to compete commercially with gasoline. However, improvements in technology to utilize wood, grass and other high cellulose containing biomass for the production of ethanol would be valuable to the art for production of a less expensive and cleaner fuel source.

In addition to biomass coversion, cellulose degrading enzymes find utility in a variety of other industrial products and processes including: textile finishing, production of detergent additives, food and beverage processing, feed additives, ensiling and fermentation processes.

Current methods for the production of cellulose degrading enzymes are generally believed to be limiting to the further development of a lignocellulosic ethanol industry. Filamentous fungi are well known for the production of industrial cellulases. However, economical production of cellulase is compounded by the relatively slow growth rates of cellulase producing fungi, the long times required for cellulase induction an the high value of the product ethanol.

Recently, genes encoding cellulose degrading enzymes have been cloned from a variety of cellulytic bacteria and fungi. Cloned genes encoding cellulases having very high specific activities over a broad pH range in addition to high thermostability are considered most desirable for bioethanol derived processes.

Recombinant bacterial or fungal hosts producing cellulose degrading enzymes have been the focus of recent efforts for the production of various cellulase preparations. However, production of cellulases in plants may find use in the art.

Since one of the major components of plants is cellulose, it would be expected that the production of cellulose degrading enzymes in plants cells may have detrimental effects to the host organism. However, by compartmentalizing the expressed cellulose degrading enzyme in a plant organelle, for example in a plastid, any detrimental effects of cellulase enzyme expression may be overcome. Furthermore, utilization of a cellulose degrading enzyme with a high temperature and/or pH optimum may also provide safeguards for the expression of such enzymes in plants that are grown at ambient temperatures.

Plant plastids (chloroplasts, amyloplasts, elaioplasts, chromoplasts, etc.) are the major biosynthetic centers that, in addition to photosynthesis, are responsible for production of industrially important compounds such as amino acids, complex carbohydrates, fatty acids, and pigments. Plastids are derived from a common precursor known as a proplastid and thus the plastids present in a given plant species all have the same genetic content. Plant cells contain 500–10,000 copies of a small 120–160 kilobase circular genome, each molecule of which has a large (approximately 25 kb) inverted repeat. Thus, it is possible to engineer plant cells to contain up to 20,000 copies of a particular gene of interest which potentially can result in very high levels of foreign gene expression. In addition, plastids of most plants are maternally inherited. Consequently, heterologous genes expressed in plastids are not pollen disseminated, therefore, a trait introduced into a plant plastid will not be transmitted to wild-type relatives by cross-fertilization. Thus, the plastids of higher plants are an attractive target for genetic engineering.

Several plastid expression systems have been developed utilizing regulatory elements derived from genes highly expressed in plant plastids. For example, promoters commonly employed to express genes in plastids are derived from the promoter regions of the 16S ribosomal RNA operon (Prrn), from the promoter region of the gene encoding for a core protein of photosystem II, the D1thylakoid membrane protein (PpsbA), or from the promoter region of the ribulose 1,5-bisphosphate carboxylase gene (PrbcL).

In addition, a totally heterologous expression system has been developed to express DNA sequences in plant plastids (McBride et al U.S. Pat. No. 5,576,198, the entirety of which is incorporated herein by reference). This system is a two component system. The first component is a plastid transgene driven by a T7 bacteriophage gene 10 promoter/leader sequence. The second component is a nuclear gene encoding the T7 RNA polymerase that is targeted to the plastid compartment. This two component expression system allows for the controlled, high level expression of DNA sequences in the plant plastid.

Utilizing high-level plastid expression offers an attractive opportunity for the expression of industrial proteins, such as thermophilic cellulases and related thermophilic polysaccharide hydrolyzing enzymes (i.e., cellobiohydrolase, xylanase, hemicellulase) in plant plastids. Expression of such enzymes in plant plastids provides an alternative source for the production of polysaccharide degrading enzymes utilized for industrial products/processes (textile finishing, detergents, food and beverage processing, feed additives, ensiling, pulping, paper making, and biomass conversions). Also, the expression of thermophilic cellulases and related cellulose degrading enzymes in plant plastids provides an alternative or supplementary method for degrading endogenous cellulose contained in plant tissues and releasing the stored carbon (as monosaccharides) for subsequent fermentative processes. In addition, plastid sequestration (isolation from the substrate) and the high temperature optimum (versus low activity at ambient temperatures) of the thermophilic cellulase provide two internal safeguards for protecting the plant from the intrinsic enzyme activity during critical plant growth and development stages.

Thus, expression of thermophilic cellulose degrading enzymes in plant plastids offers the opportunity for an less expensive and abundant source of cellulose degrading enzymes.

RELEVANT LITERATURE

Mohaghegi et al. (1986) *Int J Syst Bacteriol* 36:435–443 reports the identification of *Acidothermus cellulolyticus* ATCC 43068. Himmel et al. U.S. Pat. No. 5,275,944 and Thomas et al. U.S. Pat. No. 5,536,655 report the identification of thermostable cellulases from *Acidothermus cellulolyticus* ATCC 43068 and cloning of nucleic acid sequences encoding for the E1 β-1,4-endoglucanase (cellulase) respectively. Henrissat and Bairoch (1996) *Biochem J* 316:695–696 reports E1 cellulase as a member of family five of the glycosyl hydrolases, and Sakon et al. (1996) *Biochemistry* 35:10648–10660 reports the three-dimentional structure of E1 cellulase.

McBride et al. U.S. Pat. No. 5,576,198 and McBride et al. (1994) *Proc Natl Acad Sci* 91:7301–7305 reports the plastid expression system based on a two component system utilizing a nuclear encoded T7 polymerase targeted to the plastid which activates a transgene controlled by the T7 bacteriophage gene 10 promoter. Svab et al. (1990) *Proc Natl Acad Sci* 87:8526–8530 reports standard chloroplast transformation methods.

SUMMARY OF THE INVENTION

By this invention, a method is disclosed whereby constructs encoding a cellulose degrading enzyme can be produced in plant cells. In one embodiment of the present invention, methods are disclosed for the high level expression of a cellulose degrading enzyme in plant plastids.

The method provided for high level expression of E1 cellulase in plant plastids offers a novel means for the production of polysaccharide hydrolyzing enzymes (cellulases, cellobiohydrolases, xylanases, hemicellulases). The method generally comprises growing a plant having integrated into its plastid genome a construct comprising as operably linked components in the 5' to 3' direction of transcription, a transcription initiation region functional in a plant plastid and a DNA encoding a polysaccharide hydrolyzing enzyme (cellulase)and a transcription termination sequence.

BRIEF DESCRIPTION OF THE DRAWINGS

FIG. 1 also shows a schematic representation of the site of homologous recombination in the plastid genome. The upper line represents the transgene encoding the E1 cellulase, aadA (strep/spec) marker gene for selection of plastid transformants and plastid homology sequences. The middle line represents the region of the chloroplast genome for integration of the transgene, and the bottom line represents the nucleic acid probe used in Southern hybridization for determination of plastid transformants.

DETAILED DESCRIPTION OF THE INVENTION

Figure 1:
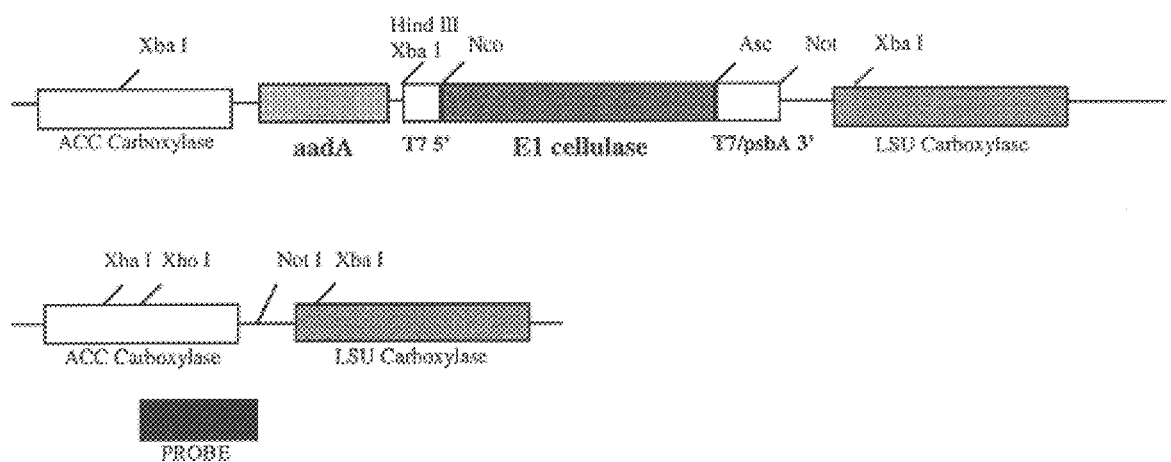
FIG. 1 shows a schematic representation of the primary DNA vector pCGN6115 for plant plastid transformation.

In accordance with the subject invention, plastid expression constructs are provided which generally comprise a promoter functional in a plant plastid, a DNA sequence encoding a thermophilic polysaccharide hydrolyzing enzyme (cellulase, cellobiohydrolase, xylanase, hemicellulse) and a transcription termination region capable of terminating transcription in a plant plastid. These elements are provided as operably joined components in the 5' to 3' direction of transcription.

The polysaccharide (cellulose) hydrolyzing enzyme of the present invention is preferably obtained from a non-plant source.

In the examples described herein, a thermophilic E1 cellulase from *Acidothermus cellulolyticus* is employed in constructs to direct expression from the plastid of plant cells. Furthermore, transplastomic tobacco plants expressing E1 cellulase demonstrate a high level of expression of the cellulase enzyme.

In addition, the expressed enzyme demonstrates similar enzymatic characteristics as the extracted wild type enzyme. For example, in the examples provided below, crude protein extracts containing the expressed cellulase from homoplasmic tobacco plants exhibits a higher activity at 80° C. than at 55° C. Thus, a thermophilic cellulase expressed from the plant plastid as described in the instant invention exhibits the same thermophilic properties as the wild type cellulase which has a temperature optimum of 83° C. (described in U.S. Pat. No. 5,536,655, the entirety of which is incorporated herein by reference). A thermophilic cellulase with increased activity above 45° C. provides an safeguard against cellulase activity during cultivation of the transformed plant in a production field. Prefered would be cellulases with activities optimized about or above 55° C.

An artisan skilled in the art to which the present invention pertains will recognize that enzymes from other sources may be utilized in plastid expression constructs of the present invention. For example, DNA sequences encoding for other polysaccharide hydrolyzing enzymes such as those from *Thermomonospora fusca* (See, e.g., Wilson (1992) *Crit. Rev. Biotechnol.* 12:45–63) may be used in the expression constructs of the present invention.

Alternatively, the constructs of the present invention may be integrated into the host plant cells nuclear genome, and the enzyme is targeted to a cellular organelle. For example, sequences directing the expressed enzyme to the vacuole may be employed, as well as sequences directing the transport to the plastid. Such plastid transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481. The protein signal for targeting to vacuoles may be provided from a plant gene which is normally transported across the rough endoplasmic reticulum, such as the 32 amino acid N-terminal region of the metallocarboxypeptidase inhibitor gene from tomato (Martineau et al. (1991) *Mol. Gen. Genet.* 228 :281–286). In addition to the signal sequence, vacuolar targeting constructs also encode a vacuolar localization signal (VLS) positioned at the carboxy terminus of the encoded protein. Appropriate signal sequences and VLS regions may be obtained from various other plant genes and may be similarly used in the constructs of this invention. Numerous vacuolar targetting peptides are known to the art, as are reviewed in Chrispeels et al., Cell (1992) 68:613–616.

In developing the constructs the various fragments comprising the regulatory regions and open reading frame may be subjected to different processing conditions, such as ligation, restriction enzyme digestion, PCR, in vitro mutagenesis for improved enzymes, linkers and adapters addition, and the like. Thus, nucleotide transitions, transversions, insertions, deletions, or the like, may be performed on the DNA which is employed in the regulatory regions or the DNA sequences of interest for expression in the plastids. Methods for restriction digests, Klenow blunt end treatments, ligations, and the like are well known to those in the art and are described, for example, by Maniatis et al. (in *Molecular cloning: a laboratory manual* (1989) Cold Spring Harbor Laboratory Press, Cold Spring Harbor, N.Y.).

During the preparation of the constructs, the various fragments of DNA will often be cloned in an appropriate cloning vector, which allows for amplification of the DNA, modification of the DNA or manipulation of the DNA by joining or removing sequences, linkers, or the like. Preferably, the vectors will be capable of replication to at least a relatively high copy number in *E. coli*. A number of vectors are readily available for cloning, including such vectors as pBR322, vectors of the pUC series, the M13 series vectors, and pBluescript vectors (Stratagene; La Jolla, Calif.).

In order to provide a means of selecting the desired plant cells, vectors for plastid transformation typically contain a construct which provides for expression of a selectable marker gene. Marker genes are plant-expressible DNA sequences which express a polypeptide which overcomes a natural inhibition by, attenuates, or inactivates a selective substance, i.e., antibiotic, herbicide etc.

Alternatively, a marker gene may provide some other visibly reactive response, i.e., may cause a distinctive appearance or growth pattern relative to plants or plant cells not expressing the selectable marker gene in the presence of some substance, either as applied directly to the plant or plant cells or as present in the plant or plant cell growth media.

In either case, the plants or plant cells containing such selectable marker genes will have a distinctive phenotype for purposes of identification, i.e., they will be distinguishable from non-transformed cells. The characteristic phenotype allows the identification of cells, cell groups, tissues, organs, plant parts or whole plants containing the construct.

Detection of the marker phenotype makes possible the selection of cells having a second gene to which the marker gene has been physically linked. This second gene typically comprises a desirable phenotype which is not readily identifiable in transformed cells, but which is present when the plant cell or derivative thereof is grown to maturity, even under conditions wherein the selectable marker phenotype itself is not apparent.

The use of such a marker for identification of plant cells containing a plastid construct has been described by Svab et al. (1993, supra). In the examples provided below, a bacterial aadA gene is expressed as the marker under the regulatory control of chloroplast 5' promoter and 3' transcription termination regions, specifically the regulatory regions of the psbA gene (described in Staub et al., *EMBO J.* (1993) 12(2):601–606). Numerous additional promoter regions may also be used to drive expression of the selectable marker gene, including various plastid promoters and bacterial promoters which have been shown to function in plant plastids.

Expression of the aadA gene confers resistance to spectinomycin and streptomycin, and thus allows for the identification of plant cells expressing this marker. The aadA gene product allows for continued growth and greening of cells whose chloroplasts produce the selectable marker gene product. Cells which do not contain the selectable marker gene product are bleached. Selection for the aadA gene marker is thus based on identification of plant cells which are not bleached by the presence of streptomycin, or more preferably spectinomycin, in the plant growth medium.

A number of markers have been developed for use with plant cells, such as resistance to chloramphenicol, the aminoglycoside G418, hygromycin, or the like. Other genes which encode a product involved in chloroplast metabolism may also be used as selectable markers. For example, genes which provide resistance to plant herbicides such as glyphosate, bromoxynil or imidazolinone may find particular use. Such genes have been reported (Stalker et al., *J. Biol. Chem.* (1985) 260:4724–4728 (glyphosate resistant EPSP); Stalker et al., *J. Biol. Chem.* (1985) 263:6310–6314 (bromoxynil resistant nitrilase gene); and Sathasivan et al., *Nucl. Acids Res.* (1990) 18:2188 (AHAS imidazolinone resistance gene)).

Methods of plant nuclear transformation and selection which employ a biolistic, or bombardment, method to transfer the target DNA constructs to plant cells may also be used in the instant invention. Such methods are particularly useful in transformation of plant cells which are less susceptible to Agrobacterium-mediated transformation methods. Bombardment tranformation methods are described in Sanford et al. (1991) *Technique* 3:3–16; Klein et al. (1992) *Bio/Technology* 10:286–291

Generally in transformation of plant cells target explants are incubated with the transformed Agrobacterium, for example as described by Horsch et al. (*Science* (1985) 227:1229–1232), or bombarded with DNA coated particles. The plant cells are then grown in an appropriate medium to selectively culture those plant cells which have obtained the desired constructs. Once callus forms, shoot formation can be encouraged by employing the appropriate plant hormones in accordance with known methods and the shoots transferred to rooting medium for regeneration of plants. The plants may then be grown and either pollinated with the same transformed strain or different strains. For production of a homozymgous line, self pollination is used.

Stable transformation of tobacco plastid genomes by particle bombardment is reported (Svab et. al. (1990), supra) and Svab et al. (1993), supra). The methods described therein may be employed to obtain plants homoplasmic for plastid expression constructs.

Generally, bombarded tissue is cultured for approximately two days on a cell division-promoting media, after which the plant tissue is transferred to a selective media containing an inhibitory amount of the particular selective agent, as well as the particular hormones and other substances necessary to obtain regeneration for that particular plant species. Shoots are then subcultured on the same selective media to ensure production and selection of homoplasmic shoots.

Homoplasmy is verified by Southern analysis for plants transplastomic for the gene encoding the E1 cellulase. In the examples provided below, Xba I-digested total cellular DNA is tested with a radio labelled probe, specifically, a part of the plastid targeting fragment, including the aadA marker gene, and sequence of the integration region containing the acetyl CoA carboxylase DNA sequence. Southern blot analysis with this probe confirms the integration of the chimeric E1 cellulase gene in the tobacco plastid genome to yield transplastome lines.

Where transformation and regeneration methods have been adapted for a given plant species, either by Agrobacterium-mediated transformation, bombardment or some other method, the established techniques may be modified for use in selection and regeneration methods to produce plastid-transformed plants. For example, the methods described herein for tobacco are readily adaptable to other solanaceous species, such as tomato, petunia and potato.

For transformation of soybean and other plant species, particle bombardment as well as Agrobacterium-mediated nuclear transformation and regeneration protocols have been described (Hinchee et al. U.S. Pat. No. 5,416,011, and Christou et al. U.S. Pat. No. 5,015,580). The skilled artisan will recognize that protocols described for soybean transformation may be used and adapted to other plant species.

In Brassica, Agrobacterium-mediated transformation and regeneration protocols generally involve the use of hypocotyl tissue, a non-green tissue which might contain a low plastid content. Thus, for Brassica, preferred target tissues would include microspore-derived hypocotyl or cotyledonary tissues (which are green and thus contain numerous plastids) or leaf tissue explants. While the regeneration rates from such tissues may be low, positional effects, such as seen with Agrobacterium-mediated transformation, are not expected, thus it would not be necessary to screen numerous successfully transformed plants in order to obtain a desired phenotype.

For cotton, transformation of *Gossypium hirsutum* L. cotyledons by co-cultivation with *Agrobacterium tumefaciens* has been described by Firoozabady et al., *Plant Mol. Bio.* (1987) 10:105–116 and Umbeck et al., *Bio/Technology* (1987) 5:263–266. Again, as for Brassica, this tissue may contain insufficient plastid content for chloroplast transformation. Thus, as for Brassica, an alternative method for transformation and regeneration of alternative target tissue containing chloroplasts may be desirable, for instance targeting green embryogenic tissue.

Other plant species may be similarly transformed using related techniques. Alternatively, microprojectile bombardment methods, such as described by Klein et al. (*Bio/Technology* 10:286–291) may also be used to obtain nuclear transformed plants comprising the viral single subunit RNA polymerase expression constructs described herein. Cotton transformation by particle bombardment is reported in WO 92/15675, published Sep. 17, 1992. Plants for the practice of the present invention include, but are not limited to, soybean, cotton, alfalfa, oil seed rape, flax, tomato, sugar beet, sunflower, potato, tobacco, maize, wheat, rice and lettuce.

The vectors for use in plastid transformation preferably include means for providing a stable transfer of the plastid expression construct and selectable marker construct into the plastid genome. This is most conveniently provided by regions of homology to the target plastid genome. The regions of homology flank the construct to be transferred and provide for transfer to the plastid genome by homologous recombination, via a double crossover into the genome. The complete DNA sequence of the plastid genome of tobacco has been reported (Shinozaki et al., *EMBO J.* (1986) 5:2043–2049). Complete DNA sequences of the plastid genomes from liverwort (Ohyama et al., *Nature* (1986) 322:572–574) and rice (Hiratsuka et al., *Mol. Gen. Genet.* (1989) 217:185–194), have also been reported.

Where the regions of homology are present in the inverted repeat regions of the plastid genome (known as IRA and IRB), two copies of the transgene are expected per transformed plastid. The regions of homology within the plastid genome are approximately 1 kb in size. Smaller regions of homology may also be used, and as little as 100 bp can provide for homologous recombination into the plastid genome. However, the frequency of recombination and thus the frequency of obtaining plants having transformed plastids decreases with decreasing size of the homology regions.

Examples of constructs having regions of homology the plastid genome are described in Svab et. al. (1990 supra), Svab et al. (1993 supra) and Zoubenko et al. (*Nuc Acid Res* (1994) 22(19):3819–3824). In the examples provided herein, the flanking tobacco plastid homology regions of the plastid expression construct direct the insertion of an E1 cellulase transgene into the tobacco chloroplast genome between acetyl CoA carboxylase (ORF512) and the large subunit of RuBisCo (rbcL). Such regions of homology are described in Svab and Maliga (1993) supra. Since integration into the plastid genome occurs by homologous recombination and the target site is not in an inverted repeat region of the plastid genome, one copy of the transgene per plastid genome is expected. Selection is made for the spectinomycin resistance marker phenotype expressed by the aadA gene.

The invention now being generally described, it will be more readily understood by reference to the following examples which are included for purposes of illustration only and are not intended to limit the present invention.

EXAMPLES

Example 1

Construct Preparation

Constructs and methods for use in transforming the plastids of higher plants are described in Zoubenko et al. (*Nuc Acid Res* (1994) 22(19):3819–3824), Svab et al. (*Proc. Natl. Acad. Sci.* (1990) 87:8526–8530 and *Proc. Natl. Acad. Sci.* (1993) 90:913–917) and Staub et al. (*EMBO J.* (1993) 12:601–606). The complete DNA sequences of the plastid genome of tobacco are reported by Shinozaki et al. (*EMBO J.* (1986) 5:2043–2049). All plastid DNA references in the following description are to the nucleotide number from tobacco.

A vector was prepared to direct the expression of the Acidothermus E1 β-1,4-endoglucanase in plant plastids. The plasmid pMPT4, a pGEM (Clonetech) derivative containing the entire Acidothermus E1 cellulase coding sequence (U.S. Pat. No. 5,536,655) and flanking regions on a 3.7 kb Pvu I genomic DNA fragment, was digested with the restriction endonuclease sites SacII and Asp718 to remove the coding sequence for the mature E1 cellulase protein. This fragment was cloned into the same restriction sites of the plasmid pBCSK+ (Stratagene) to create the vector pCGN6063. This plasmid was digested with SacI and SacII and a double-stranded oligonucleotide sequence, 5'GGAGCTGCGTCACCATGGCGGGA-3', was inserted to introduce an NcoI site-derived ATG translational start codon fused to the 60,000 mol wt mature sequence (minus the endogeneous bacterial signal peptide amino acid sequence) of the E1 β-1,4-endoglucanase polypeptide, creating the construct pCGN6067. The E1 gene was excised from pCGN6067 as an Nco I to Asc I DNA segment and cloned into the T7 promoter expression cassette pCGN5063 to create the construct pCGN6108. This plasmid contains the plastid expression regulatory elements of the T7 bacteriophage promoter operably linked to the mature protein portion of the E1 coding sequence and psbA transcription termination region. The chimeric cellulase expression cassette was excised as a Hind III to Not I DNA fragment and cloned into the tobacco chloroplast homology vector, pCGN6043 in the same restriction sites to create the construct pCGN6115. The homology sequences employed in the vector direct the integration of the E1 cellulase gene and aadA marker transgene to the region between the rbcL and ORF512 sequences (described in Svab et al., (1993) supra). The construct pCGN6115 (FIG. 1) was used to transform tobacco plants to direct the transformation to homoplasmy and plastid expression of the E1 β-1,4-endoglucanase encoding gene in the plant plastid.

EXAMPLE 2

Plant Plastid Transformation

Tobacco plants transformed to express T7 polymerase from the nuclear genome and targeted to the plant plastid are obtained as described in McBride et al U.S. Pat. No. 5,576,198. Transgenic tobacco plants homozygous for the plastid targeted T7 polymerase are used for plastid transformation using particle bombardment.

Tobacco plastids are transformed by particle gun delivery of microprojectiles. Since integration into the plastid genome occurs by homologous recombination and the target site is between the acetyl CoA carboxylase and the large subunit of RuBisCo (rbcL), a single copy of the transgene is expected per plastid genome (Svab et al. (1993) supra).

Tobacco seeds (N. tabacum v. Xanthi N/C) homozygous for pCGN4026 (McBride et al., U.S. Pat. No. 5,576,198) T-DNA are surface sterilized in a 50% chlorox solution (2.5% sodium hypochlorite) for 20 minutes and rinsed 4 times in sterile $H_2O$. The seeds are then plated aseptically on a 0.2× MS salts media and allowed to germinate. The seedlings are grown on agar solidified MS media with 30 g/l sucrose (Murashige and Skoog (1962) *Physiol. Plant* 15:493–497).

Tungsten microprojectiles (1.0 μm) are coated with DNA, such as the T7/E1 cellulase expression construct, pCGN6115, and the coated microprojectiles used to bombard mature leaves, placed abaxial side up on RMOP media (MS salts, 1 mg/l BAP, 0.1 mg/l NAA, 30 g/l sucrose and 0.7% phytager) (Svab et al. (1990) supra) using the Bio-Rad PDS 1000/He bombardment system (Sanford et al. (1991) *Technique* 3:3–16; Klein et al. (1992) *Bio/Technology* 10:286–291). Development of transformed plants on RMOP media supplemented with 500 mg/l spectinomycin dihydrochloride and subsequent subcloning on the same selective medium is conducted according to Svab et al. (1990); Svab and Maliga (1993); supra). Selected plants are rooted in MS media containing 1 mg/l IBA, 500 mg/l spectinomycin dihydrochloride and 0.6% phytagar.

EXAMPLE 3

Analysis of Cellulase Expression in Plastids

Following plastid transformation as described above, five independently isolated homoplasmic lines generated in the nuclear encoded T7 RNA polymerase producing background were generated. A schematic of pCGN6115 construct and a representation of incorporation into the tobacco plastid genome is shown in FIG. 1. The upper line represents the incoming DNA donated from pCGN6115 and the middle line represents the integration target region. Expected sizes for XbaI fragments are shown for the incoming DNA as well as for wild type DNA. As there is no XbaI site on the 5' end of the incoming DNA the combined size of the two chimeric genes is indicated. Also shown in FIG. 1 is the location of the probe used for Southern analysis. Homoplasmy was determined by Southern blot analysis as shown in FIG. 2.

To confirm homoplasmy by Southern hybridization, total plant cellular DNA is prepared as described by Bernatzky and Tanksley ((1986) *Theor Appl Genet.* 72:314–321). Approximately 3 μg DNA for each sample is digested with XbaI, electrophoresed through 0.7% agarose, transferred to Nytran+ (Schleicher and Schuell). The filters were hybridized in buffer (50% formamide, 6× SSC, 5× Denhardt's solution, 0.5% SDS, 150 μg/ml Salmon sperm DNA) at 42° C. with alpha $^{32}$P-dCTP labeled probe. The hybridization probe was prepared from a nucleic acid sequences spanning the the integration zone. This DNA sequence contains approximately 50% of the native chloroplast gene acetyl CoA Carboxylase and some flanking intergenic sequence, and is derived as a NotI/XhoI fragment from pCCN6042, a precursor plasmid containing only the tobacco plastid homology sequences present in plasmid pCGN6115.

Figure 2:
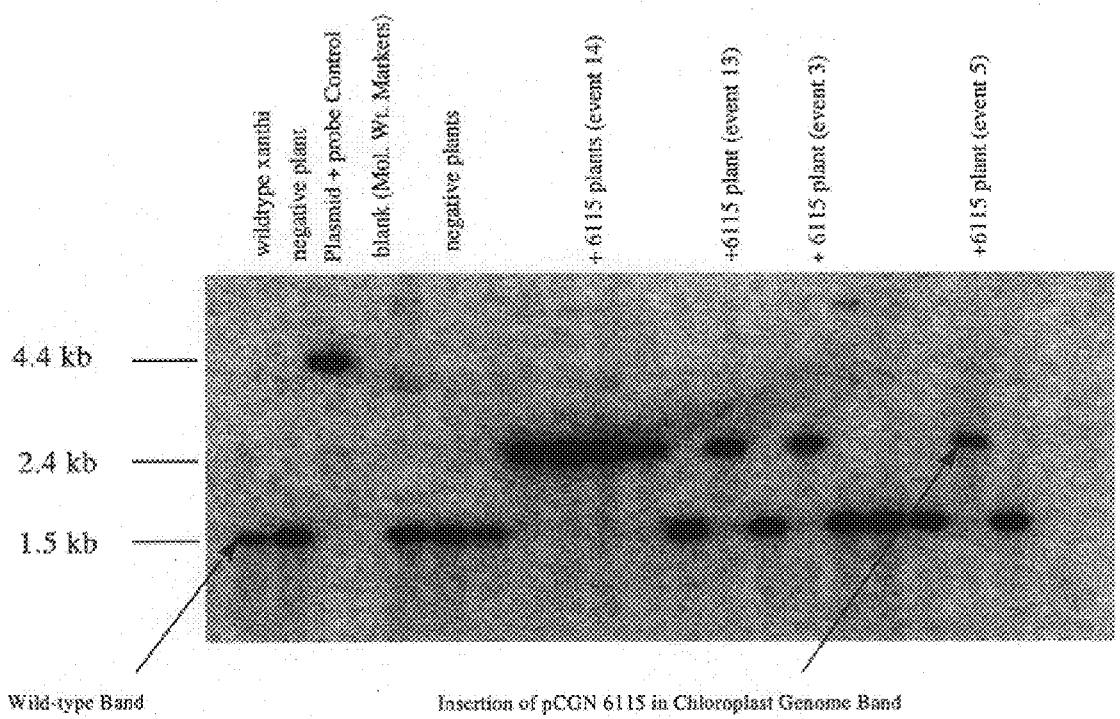
FIG. 2 shows the result of the Southern hybridization utilizing the probe depicted. The wild type band is in lane 1. A plasmid (pCGN6115) control is in lane 3. Several subclones of the same transgenic events were analyzed on the same blot. Each subclone was regenerated from the same inital transformant. For example, in event 6115-14, there are 4 subclones of the same event, all are homplasmic for the inserted genes. Some subclones are wild type in the other events.

The results of the Southern hybridization are shown in FIG. 2. Homoplasmic lines are identified which contain the E1 cellulase and aadA coding sequences. Non-transformed control tobacco lines (wild-type Xanthi) probed with the 6042 DNA fragment hybridize with a 1.5 kb DNA fragment, while homoplasmic tobacco lines containing the E1 cellulase and aadA sequences hybridize with a 2.5 kb DNA fragment. Transplastomic lines which are heteroplasmic demonstrate a hybridization pattern containing both the wild-type DNA fragment, 1.5 kb, and the homoplasmic DNA fragment, 2.5 kb. The difference in band size between the transgenic plants and wild type is the presence of the aadA resistance gene and its regulatory sequences in the transgenic plants. This adds approximately 1 kb to the wild type band.

To demonstrate that the homoplasmic 6115 tobacco lines express the E1 β-1,4-endoglucanase, Western blot analysis was performed using total soluble leaf protein. Leaf protein was extracted as follows: 200 mg mature leaf samples were frozen in liquid N2 and ground in 0.08 ml extraction buffer containing 0.1M NaPO$_4$ pH 6.8, 0.15M NaCl, 0.01M EDTA, 0.01M DTT, 0.01M thiourea, 0.3% Tween-20, 0.05% Triton-X100. Protein concentrations were determined by Bradford assay. Protein samples were combined with an equal volume of 2× Laemmli sample buffer (Laemmli (1970) *Nature* 227:680–685) and boiled prior to loading onto 10% Laemmli gels. Approximately 40 ug of total leaf protein was loaded/lane.

Figure 3:
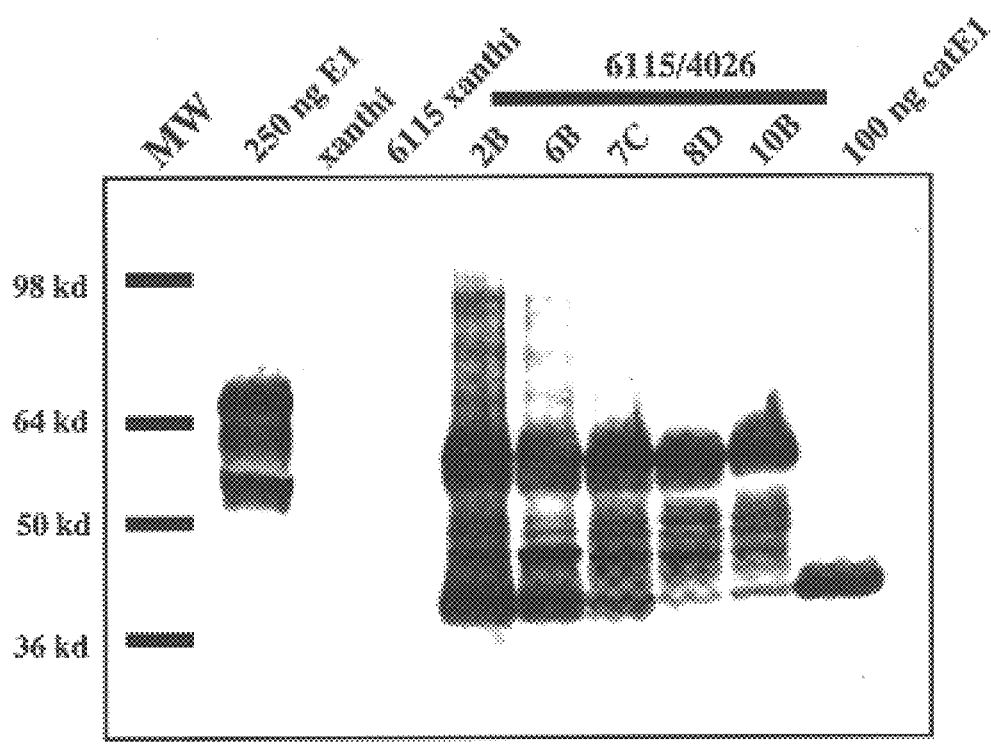
FIG. 3 shows the results of Western hybridization of total soluble leaf protein extracted from homoplasmic tobacco lines transformed with the pCGN6115 construct using monoclonal antibodies raised to purified *Acidothermus cellulolyticus* E1 β-1,4-endoglucanase.

Results of the Western blot analysis (FIG. 3) using monoclonal antibodies raised against the Acidothermus E1 cellulase demonstrate that the E1 protein is expressed in all homoplasmic 6115 lines examined. 250 ng of E1 cellulase purified from Strepromyces was loaded onto the first lane. This protein runs as multiple forms on a denaturing gel, the highest form being 72,000 molecular weight as this form includes the signal peptide for secretion. The mature form of the enzyme is around 60 kd. The second lane contains control tobacco tissue. The third lane contains an extract from a 6115 homoplasmic plant that does not contain the T7 RNA polymerase to activate E1 cellulase expression in the plastid. Lanes 4–8 are independent 6115 homoplasmic lines in a 4026 xanthi background. The 4026 construct expresses the plastid-targeted T7 RNA polymerase that activates E1 cellulase expression in the plastid. The major protein band at 60 kd constitutes the mature E1 cellulase. Lane 9 shows 100 ng of the *E. coli* purified catalytic form of the E1 cellulase minus the cellulose binding domain (CBD).

The Acidothermus E1 cellulase purified from recombinant Streptomyces runs as multiple forms on a denaturing gel, the highest form being 72,000 molecular weight as this form includes the endogeneous signal peptide required for secretion of the enzyme from the bacterium. The mature form of the enzyme is around 60 kilodaltons. Thus, as can be noted from FIG. 3, E1 cellulase expressed in plant plastids as a 60 kd mature form and can be converted to the 40 kd catalytic domain form, presumably by proteolytic processing in vivo. Furthermore, from the results of the Western blot analysis it can be estimated that protein expression of E1 β-1,4-endoglucanase is approximately 1% of the total soluble plant protein in leaves of transplastomic tobacco lines.

Crude total soluble leaf protein from homoplasmic 6115 tobacco lines expressing E1 cellulase were further analyzed for cellulase activity. Since Acidothermus E1 cellulase $V_{max}$ is near maximal approaching 80° C, experiments were carried out at 55° C. and 80° C. Protein extracts (approximately 12 ug total leaf protein) were tested in reactions to measure the hydrolysis of the fluorogenic substrate 4-methylumbelliferyl-β-D-cellobioside (MUC) as described in Laymon et al. (1996) *Applied Biochem. Biotechnol.* 57/58:389–397. The results are listed in Table 1.

TABLE 1

| Line | 60 min @ 55° C. pM Mu/μg/min | 60 min @ 80° C. pM Mu/μg/min | Fold Increase at 80° C. |
|---|---|---|---|
| 6115-7 | 392,063 | 2,432,540 | 6.20 |
| 6115-8 | 145,294 | 747,059 | 5.14 |
| 6115-10 | 39,706 | 222,549 | 5.60 |
| 6115-11 | 88,596 | 574,561 | 6.49 |
| Xanthi (control) | n/a | 13,636 | n/a |

The above results clearly indicate that the cellulase expressed in plant plastids has a higher level of activity at 80° C. Increases in enzyme activity of 5 to 6 fold are observed when crude extracts are incubated with MUC at 80° C. than the cellulase activities obtained in incubations at 55° C. Thus, the cellulase expressed in plant plastids demonstrates similar kinetic characteristics as the wild type enzyme isolated from *Acidothermus cellulolyticus*.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A construct comprising the following as operably joined components in the 5' to 3' direction of transcription:
   (a) a promoter functional in a plant cell;
   (b) a DNA sequence encoding the E1 cellulase from *Acidothermus cellulolyticus*; and
   (c) a transcription termination region.

2. A construct according to claim 1 wherein said promoter is functional in a plant plastid.

3. The construct according to claim 2 wherein said plant plastid is a chloroplast.

4. The construct according to claim 1 further comprising a targeting sequence capable of directing transport to a cellular organelle.

5. The construct according to claim 4 wherein said targeting sequence directs transport to a vacuole.

6. The construct according to claim 4 wherein said targeting sequence directs transport to a plastid.

7. The construct according to claim 1 wherein said enzyme is active at temperatures above about 45° C.

8. The construct according to claim 7 wherein activity of said enzyme is increased at temperatures above about 45° C.

9. The construct according to claim 7 wherein activity of said enzyme is active at temperatures above about 55° C.

10. The construct according to claim 7 wherein activity of said enzyme is active at temperatures above about 80° C.

11. A plant cell containing the construct according to claim 1.

12. A plant cell according to claim 11 wherein said construct is integrated in the nuclear genome of said cell.

13. A plant cell according to claim 11 wherein said construct is integrated in the genome of plastids of said cell.

14. A plant, plant seed or plant part comprising a cell according to either one of claim 12 or claim 13.

15. A method for altering cellulose content in plant tissue comprising the steps of growing a plant comprising cells having a construct with the following operably joined components in the 5' to 3' direction of transcription; i) a promoter functional in a plant cell; ii) a DNA sequence encoding the E1 cellulase from *Acidothermus cellulolyticus*; and iii) a transcription termination region, under conditions whereby a said enzyme is expressed in cells of said plant.

16. The method according to claim 15 whereby cellulose of said plant cells is degraded thereby reducing said cellulose content.

17. The method according to claim 16 whereby the digestability of plant material comprising said plant cells is improved.

18. The method according to claim 15 wherein said promoter is functional in a plant plastid.

19. The method according to claim 16 wherein said plant plastid is a chloroplast.

20. The method according to claim 15 further comprising a targeting sequence capable of directing transport to a cellular organelle.

21. The method according to claim 15 wherein said targeting sequence directs transport to a vacuole.

22. The method according to claim 15 wherein said targeting sequence directs transport to a plastid.

23. The method according to claim 15 further comprising the steps of harvesting plant material from said plant and subjecting said harvested plant material to conditions whereby the activity of said enzyme is increased and cellulose content of said plant material is reduced.

24. The method according to claim 23 wherein said activity of said enzyme is increased at temperatures above about 45° C.

25. The method according to claim 23 wherein said activity of said enzyme is increased at temperatures above about 55° C.

26. The method according to claim 23 wherein said activity of said enzyme is increased at temperatures above about 80° C.

* * * * *